(12) United States Patent
Ando et al.

(10) Patent No.: US 9,624,155 B2
(45) Date of Patent: Apr. 18, 2017

(54) IRON (III) CITRATE, SUBSTANTIALLY FREE OF BETA-IRON HYDROXIDE OXIDE

(71) Applicant: Japan Tobacco Inc., Tokyo (JP)

(72) Inventors: Koji Ando, Takatsuki (JP); Naoki Manta, Takatsuki (JP)

(73) Assignee: Japan Tobacco Inc., Tokyo (JP)

( * ) Notice: Subject to any disclaimer, the term of this patent is extended or adjusted under 35 U.S.C. 154(b) by 0 days.

(21) Appl. No.: 14/184,062

(22) Filed: Feb. 19, 2014

(65) Prior Publication Data

US 2015/0025138 A1 Jan. 22, 2015

Related U.S. Application Data

(63) Continuation of application No. 13/352,423, filed on Jan. 18, 2012, now abandoned.

(60) Provisional application No. 61/438,303, filed on Feb. 1, 2011.

(30) Foreign Application Priority Data

Jan. 18, 2011 (JP) ................. 2011-007887

(51) Int. Cl.
*C07C 51/41* (2006.01)
*C07C 59/265* (2006.01)
*C07F 15/02* (2006.01)

(52) U.S. Cl.
CPC .......... *C07C 51/412* (2013.01); *C07C 59/265* (2013.01); *C07F 15/02* (2013.01)

(58) Field of Classification Search
CPC ........ C07C 51/418; C07C 51/41; C07F 15/02
See application file for complete search history.

(56) References Cited

U.S. PATENT DOCUMENTS

| | | | |
|---|---|---|---|
| 3,591,616 | A | 7/1971 | Baldt et al. |
| 5,206,265 | A | 4/1993 | Vidic et al. |
| 5,753,706 | A | 5/1998 | Hsu |
| 6,903,235 | B2 | 6/2005 | Hsiao et al. |
| 2005/0080283 | A1 | 4/2005 | Hsiao et al. |
| 2006/0020026 | A1* | 1/2006 | Kwok ............ A61K 31/295 514/502 |
| 2008/0274210 | A1 | 11/2008 | Chan et al. |
| 2012/0115945 | A1 | 5/2012 | Le et al. |
| 2012/0121703 | A1 | 5/2012 | Fukushima et al. |

FOREIGN PATENT DOCUMENTS

| | | |
|---|---|---|
| CN | 1315174 | 10/2001 |
| CN | 1446790 | 10/2003 |
| CN | 1935769 | 3/2007 |
| JP | H03-502570 | 6/1991 |
| JP | 2001506262 | 5/2001 |
| WO | WO98/26776 | 6/1998 |
| WO | WO2004/007444 | 1/2004 |
| WO | WO2007/022435 | 2/2007 |
| WO | WO2007/089571 | 8/2007 |
| WO | WO2007/089577 | 8/2007 |

OTHER PUBLICATIONS

Capasso et al (Environmental Science and Technology, 2004, vol. 38, pp. 5170-5176, abstract).*
Office Action issued in Japanese Application No. 2012-007639, Jul. 27, 2015, 6 pages (and English translation).
Hsu et al., "New phosphate binding agents: ferric compounds," *J. Am. Soc. Nephrol.*, 1999, 10(6):1274-80.
Kinugasa, "New Phosphate Binders," *Current Topics*, 2003, 18(2):101-06.
Kuroda et al, "Effect of iron as a new type of phosphate binder in hemodialysis patients," *Nippon Jinzo Gakkai Shi.*, 1995, 37(8):468-73.
Silva et al., "Iron(III) citrate speciation in aqueous solution," *Dalton Trans.*, 2009, (40):8616-25.
Yang et. al., "An open-label, crossover study of a new phosphate-binding agent in haemodialysis patients: ferric citrate," *Nephrol Dial Transplant.*, 2002, 17(2):265-70.
Supplementary European Search Report issued in EP Application No. 12736578.1, dated Jan. 29, 2016, 7 pages.
Office Action issued in Japanese patent application No. 2016-043505, dated Dec. 21, 2016 (with English Translation).

* cited by examiner

*Primary Examiner* — Mark V Stevens
(74) *Attorney, Agent, or Firm* — Fish & Richardson P.C.

(57) ABSTRACT

This invention provides a method for producing high-purity iron(III) citrate substantially free of beta-iron hydroxide oxide, high-purity iron(III) citrate substantially free of beta-iron hydroxide oxide, and medical uses thereof.

16 Claims, 4 Drawing Sheets

IRON (III) CITRATE, SUBSTANTIALLY FREE OF BETA-IRON HYDROXIDE OXIDE

CROSS REFERENCE TO RELATED APPLICATIONS

This application is a continuation of U.S. application Ser. No. 13/352,423, filed Jan. 18, 2012, abandoned, which claims the benefit of priority of U.S. provisional application Ser. No. 61/438,303, filed Feb. 1, 2011, and Japanese application serial number 2011-007887, filed Jan. 18, 2011. The disclosures of the prior applications are considered part of (and are incorporated by reference in) the disclosure of this application.

TECHNICAL FIELD

The present invention relates to high-purity iron(III) citrate and a method for producing the same.

BACKGROUND ART

Patent Document 1 describes that a ferric organic compound involving an iron(III) citrate of a specific type is useful for treatment of hyperphosphatemia or other diseases.

PRIOR ART DOCUMENT

Patent Document

Patent Document 1: JP Patent Publication (Kohyo) No. 2006-518391 A

SUMMARY OF THE INVENTION

Object to be Attained by the Invention

The present invention is intended to provide a method for producing high-purity iron(III) citrate substantially free of beta-iron hydroxide oxide, high-purity iron(III) citrate substantially free of beta-iron hydroxide oxide, and medical uses thereof.

Means for Attaining the Object

The present inventors studied a variety of means for attaining the above object. As a result, the present inventors have discovered that such object could be attained by modifying the conditions used in connection with the method described in Patent Document 1 for bringing ferric chloride into contact with sodium hydroxide, thereby completing the present invention.

Specifically, the present invention is summarized as follows.

(1) High-purity iron(III) citrate substantially free of beta-iron hydroxide oxide, wherein the beta-iron hydroxide oxide content is less than 6% by weight based on the total weight thereof.

(2) The high-purity iron(III) citrate according to (1), wherein the beta-iron hydroxide oxide content is less than 2.5% by weight.

(3) The high-purity iron(III) citrate according to (1), wherein the beta-iron hydroxide oxide content is less than 1.0% by weight.

(4) The high-purity iron(III) citrate according to any of (1) to (3), wherein the molar ratio of iron(III) to citric acid is from 1:0.75 to 1:1.10.

(5) The high-purity iron(III) citrate according to (4), wherein the molar ratio of iron(III) to citric acid is from 1:0.80 to 1:0.92.

(6) The high-purity iron(III) citrate according to any of (1) to (5), wherein the percentage of iron(III) citrate dissolved within 15 minutes is 80% or more in dissolution testing conducted with the use of the first fluid of dissolution testing of the Japanese Pharmacopoeia, Fifteenth Edition as a test liquid via the paddle method at 100 rpm in accordance with the Japanese Pharmacopoeia, Fifteenth Edition.

(7) A pharmaceutical composition comprising, as an active ingredient, the high-purity iron(III) citrate according to any of (1) to (6).

(8) An agent for treatment or amelioration of hyperphosphatemia comprising, as an active ingredient, the high-purity iron(III) citrate according to any of (1) to (6).

(9) A phosphate binder comprising, as an active ingredient, the high-purity iron(III) citrate according to any of (1) to (6).

(10) An agent for reducing serum phosphorus level comprising, as an active ingredient, the high-purity iron(III) citrate according to any of (1) to (6).

(11) Powder of the high-purity iron(III) citrate according to any of (1) to (6), which has an amorphous structure.

(12) Powder of the high-purity iron(III) citrate according to any of (1) to (6), which has a specific surface area of 20 to 45 $m^2/g$.

(13) Powder of the high-purity iron(III) citrate according to (11), which has a specific surface area of 20 to 45 $m^2/g$.

(14) A pharmaceutical composition comprising, as an active ingredient, the powder according to any of (11) to (13).

(15) An agent for treatment or amelioration of hyperphosphatemia comprising, as an active ingredient, the powder according to any of (11) to (13).

(16) A method for producing iron(III) citrate comprising:
a step of forming an iron-containing precipitate comprising bringing ferric chloride into contact with sodium hydroxide for a short period of time at low temperature in an aqueous medium to form an iron-containing precipitate;
a step of generating an aqueous solution of iron(III) citrate comprising bringing citric acid into contact with the iron-containing precipitate in an aqueous medium and generating an aqueous solution of iron(III) citrate via heating; and
a step of precipitating iron(III) citrate comprising bringing the aqueous solution of iron(III) citrate into contact with an organic solvent to precipitate the iron(III) citrate.

(17) The method according to (16), wherein the step of forming iron-containing precipitate comprises bringing ferric chloride into contact with sodium hydroxide within 2 hours at a liquid temperature of 0° C. to 10° C.

(18) The method according to (16) or (17), wherein the step of generating an aqueous solution of iron(III) citrate comprises bringing citric acid into contact with the iron-containing precipitate at a liquid temperature of 60° C. to 100° C.

(19) The method according to any of (16) to (18), wherein the iron-containing precipitate is ferrihydride.

(20) Iron(III) citrate produced by the method according to any of (16) to (19).

(21) A pharmaceutical composition comprising, as an active ingredient, the iron(III) citrate according to (20).

(22) An agent for treatment or amelioration of hyperphosphatemia comprising, as an active ingredient, the iron(III) citrate according to (20).

(23) A phosphate binder comprising, as an active ingredient, the iron(III) citrate according to (20).

(24) An agent for reducing serum phosphorus level comprising, as an active ingredient, the iron(III) citrate according to (20).

(25) Powder of the iron(III) citrate according to (20), which has an amorphous structure.

(26) Powder of the iron(III) citrate according to (20), which has a specific surface area of 20 to 45 $m^2/g$.

(27) Powder of the iron(III) citrate according to (25), which has a specific surface area of 20 to 45 $m^2/g$.

(28) A pharmaceutical composition comprising, as an active ingredient, the powder according to any of (25) to (27).

(29) An agent for treatment or amelioration of hyperphosphatemia comprising, as an active ingredient, the powder according to any of (25) to (27).

(30) The pharmaceutical composition according to (7), (14), (21), or (28) for use in treatment of hyperphosphatemia.

(31) A high-purity iron(III) complex with citric acid and water substantially free of beta-iron hydroxide oxide, wherein the beta-iron hydroxide oxide content is less than 6% by weight based on the total weight thereof.

(32) The high-purity iron(III) complex with citric acid and water according to (31), wherein the beta-iron hydroxide oxide content is less than 2.5% by weight.

(33) The high-purity iron(III) complex with citric acid and water according to (31), wherein the beta-iron hydroxide oxide content is less than 1.0% by weight.

(34) The high-purity iron(III) complex with citric acid and water according to any of (31) to (33), wherein the molar ratio of iron(III) to citric acid is from 1:0.75 to 1:1.10.

(35) The high-purity iron(III) complex with citric acid and water according to any of (31) to (33), wherein the molar ratio of iron(III) to citric acid is from 1:0.80 to 1:0.92.

(36) The high-purity iron(III) complex with citric acid and water according to any of (31) to (33), which has a specific surface area of 20 to 45 $m^2/g$ and an amorphous structure.

(37) The high-purity iron(III) complex with citric acid and water according to any of (31) to (36), wherein the percentage of the high-purity iron(III) complex dissolved within 15 minutes is 80% or more in dissolution testing conducted with the use of the first fluid of dissolution testing of the Japanese Pharmacopoeia, Fifteenth Edition as a test liquid via the paddle method at 100 rpm according to the Japanese Pharmacopoeia, Fifteenth Edition.

(38) A pharmaceutical composition comprising, as an active ingredient, the high-purity iron(III) complex with citric acid and water according to any of (31) to (37).

(39) An agent for treatment or amelioration of hyperphosphatemia comprising, as an active ingredient, the high-purity iron(III) complex with citric acid and water according to any of (31) to (37).

(40) A phosphate binder comprising, as an active ingredient, the high-purity iron(III) complex with citric acid and water according to any of (31) to (37).

(41) An agent for reducing serum phosphorus level comprising, as an active ingredient, the high-purity iron(III) complex with citric acid and water according to any of (31) to (37).

(42) A method for producing an iron(III) complex with citric acid and water comprising:

a step of forming an iron-containing precipitate comprising bringing ferric chloride into contact with sodium hydroxide for a short period of time at low temperature in an aqueous medium to form an iron-containing precipitate;

a step of generating an aqueous solution of the iron(III) complex with citric acid and water comprising bringing citric acid into contact with the iron-containing precipitate in an aqueous medium and generating an aqueous solution of the iron(III) complex with citric acid and water via heating; and a step of precipitating an iron(III) complex with citric acid and water comprising bringing an aqueous solution of the iron(III) complex with citric acid and water into contact with an organic solvent to precipitate the iron(III) complex with citric acid and water.

(43) The method according to (42), wherein the step of forming iron-containing precipitate comprises bringing ferric chloride into contact with sodium hydroxide within 2 hours at a liquid temperature of 0° C. to 10° C.

(44) The method according to (42) or (43), wherein the step of generating an aqueous solution of the iron(III) complex with citric acid and water comprises bringing citric acid into contact with the iron-containing precipitate at a liquid temperature of 60° C. to 100° C.

(45) The method according to any of (42) to (44), wherein the iron-containing precipitate is ferrihydrite.

(46) An iron(III) complex with citric acid and water produced by the method according to any of (42) to (45).

(47) A pharmaceutical composition comprising, as an active ingredient, the iron(III) complex with citric acid and water according to (46).

(48) The pharmaceutical composition according to (38) or (47) for use in treatment of hyperphosphatemia.

(49) An agent for treatment or amelioration of hyperphosphatemia comprising, as an active ingredient, the iron(III) complex with citric acid and water according to (46).

(50) An agent for treating hyperphosphatemia or phosphate binder comprising, as an active ingredient, the iron(III) complex with citric acid and water according to (46).

(51) An agent for treating hyperphosphatemia or for reducing serum phosphorus level comprising, as an active ingredient, the iron(III) complex with citric acid and water according to (46).

(52) A method for treatment or amelioration of hyperphosphatemia comprising administering an effective amount of the high-purity iron(III) citrate according to any of (1) to (6) or the iron(III) citrate according to (20) to a patient or a test subject in need thereof.

(53) Use of the high-purity iron(III) citrate according to any of (1) to (6) or the iron(III) citrate according to (20) in the manufacture of a medicament for treatment or amelioration of hyperphosphatemia.

(54) The high-purity iron(III) citrate according to any of (1) to (6) or the iron(III) citrate according to (20) for use as a medicament.

(55) The high-purity iron(III) citrate according to any of (1) to (6) or the iron(III) citrate according to (20) for use in treatment or amelioration of hyperphosphatemia.

(56) A method for treatment or amelioration of hyperphosphatemia comprising administering an effective amount of powder of the high-purity iron(III) citrate according to any of (11) to (13) or powder of the iron(III) citrate according to any of (25) to (27) to a patient or a test subject in need thereof.

(57) Use of the powder of the high-purity iron(III) citrate according to any of (11) to (13) or powder of the iron(III) citrate according to any of (25) to (27) in the manufacture of a medicament for treatment or amelioration of hyperphosphatemia.

(58) Powder of the high-purity iron(III) citrate according to any of (11) to (13) or powder of the iron(III) citrate according to any of (25) to (27) for use as a medicament.

(59) Powder of the high-purity iron(III) citrate according to any of (11) to (13) or powder of the iron(III) citrate according to any of (25) to (27) for use in treatment or amelioration of hyperphosphatemia.

(60) A method for treatment or amelioration of hyperphosphatemia comprising administering an effective amount of the high-purity iron(III) complex with citric acid and water according to any of (31) to (37) or the iron(III) complex with citric acid and water according to (46) to a patient or a test subject in need thereof.

(61) Use of the high-purity iron(III) complex with citric acid and water according to any of (31) to (37) or the iron(III) complex with citric acid and water according to (46) in the manufacture of a medicament for treatment or amelioration of hyperphosphatemia.

(62) The high-purity iron(III) complex with citric acid and water according to any of (31) to (37) or the iron(III) complex with citric acid and water according to (46) for use as a medicament.

(63) The high-purity iron(III) complex with citric acid and water according to any of (31) to (37) or the iron(III) complex with citric acid and water according to (46) for use in treatment or amelioration of hyperphosphatemia.

This description includes part or all of the contents as disclosed in the descriptions and/or drawings of Japanese Patent Application No. 2011-007887 and U.S. Provisional Patent Application No. 61/438,303, which are priority documents of the present application.

Effects of the Invention

The present invention can provide a method for producing high-purity iron(III) citrate substantially free of beta-iron hydroxide oxide, high-purity iron(III) citrate substantially free of beta-iron hydroxide oxide, and medical uses thereof.

EMBODIMENTS FOR CARRYING OUT THE INVENTION

1. Iron(III) Citrate

The present invention relates to high-purity iron(III) citrate substantially free of beta-iron hydroxide oxide.

The term "iron(III) citrate" used herein refers to a complex of iron(III) (Fe(III)) with citric acid, and an embodiment thereof is a complex represented by the following molecular formula: $Fe \cdot x(C_6H_8O_7) \cdot y(H_2O)$. In the above molecular formula, x is preferably from 0.75 to 1.10, more preferably from 0.78 to 0.95, particularly preferably from 0.80 to 0.92, and most preferably from 0.81 to 0.91. According to another embodiment, x is preferably from 0.75 to 1.15, and more preferably from 0.80 to 1.10. y is preferably from 1.8 to 3.2, more preferably from 2.4 to 3.1, and particularly preferably from 2.7 to 3.1. Also, the molar ratio of iron(III) to citric acid is preferably from 1:0.75 to 1:1.10, more preferably from 1:0.78 to 1:0.95, particularly preferably from 1:0.80 to 1:0.92, and most preferably from 1:0.81 to 1:0.91. According to another embodiment, the molar ratio of iron(III) to citric acid is preferably from 1:0.75 to 1:1.15, and more preferably from 1:0.80 to 1:1.10. The molar ratio of iron(III) to water is preferably from 1:1.8 to 1:3.2, more preferably from 1:2.4 to 1:3.1, and particularly preferably from 1:2.7 to 1:3.1.

As described in detail below, the present inventors have discovered that preparation of a complex of iron(III) with citric acid according to the method described in Patent Document 1 would occasionally lead to inclusion of beta-iron hydroxide oxide ($\beta$-FeOOH), which is hardly soluble in water, as a by-product in the complex.

In contrast, the iron(III) citrate of the present invention produced by the method described below is substantially free of beta-iron hydroxide oxide. Thus, the present invention provides high-purity iron(III) citrate substantially free of beta-iron hydroxide oxide. According to an embodiment of the present invention, the iron(III) citrate is a high-purity iron(III) complex with citric acid and water substantially free of beta-iron hydroxide oxide. Thus, the iron(III) citrate of the present invention encompasses a high-purity iron(III) complex with citric acid and water substantially free of beta-iron hydroxide oxide. In the high-purity iron(III) citrate according to the present invention, the beta-iron hydroxide oxide content is preferably less than 6% by weight, more preferably 2.5% or less by weight, particularly preferably 1.0% or less by weight, and most preferably 0 to 1% by weight, relative to the total weight. In this description, the term "substantially free of beta-iron hydroxide oxide" refers to condition in which the beta-iron hydroxide oxide content is within the range described above, and the term "high-purity iron(III) citrate" refers to iron(III) citrate with a beta-iron hydroxide oxide content that is within the range described above.

It should be noted that the beta-iron hydroxide oxide content in iron(III) citrate can be determined via, for example, but is not limited to, powder X-ray diffraction.

According to an embodiment of the present invention, the iron(III) citrate and high-purity iron(III) citrate each have a specific surface area of, for example, 20 $m^2/g$ or higher, preferably 20 to 45 $m^2/g$, and more preferably 20 to 40 $m^2/g$.

A specific surface area can be measured by, for example, but is not limited to, BET surface area measurement via nitrogen gas adsorption (relative pressure: 0.05 to 0.3).

According to an embodiment of the present invention, the iron(III) citrate and high-purity iron(III) citrate are amorphous, and preferably amorphous powders. Thus, the present invention also relates to an amorphous form or amorphous powder of iron(III) citrate or high-purity iron(III) citrate having features described above and below. The term "amorphous form" used herein refers to a halo pattern having diffusive maxima observed via powder X-ray diffraction.

In addition, the percentage of the iron(III) citrate and that of high-purity iron(III) citrate according to the present invention dissolved within 15 minutes are each 80% or more, preferably 85% or more, more preferably 90% or more, and most preferably 95% or more, in dissolution testing conducted with the use of the first fluid of dissolution testing of the Japanese Pharmacopoeia, Fifteenth Edition as a test liquid via the paddle method at 100 rpm according to the Japanese Pharmacopoeia, Fifteenth Edition.

Because of such features, the iron(III) citrate and high-purity iron(III) citrate according to the present invention can exert excellent dissolution properties.

2. Method for Producing Iron(III) Citrate

The present invention also relates to a method for producing iron(III) citrate. The method of the present invention at least comprises a step of forming an iron-containing precipitate, a step of generating an aqueous solution of iron(III) citrate, and a step of precipitating iron(III) citrate. These steps are described below.

2-1. Step of Forming Iron-Containing Precipitate

This step is intended to form an iron-containing precipitate by bringing ferric chloride into contact with sodium hydroxide in an aqueous medium. An example of "contact" is dropwise addition of an aqueous solution of sodium hydroxide to an aqueous solution of ferric chloride, but not limited thereto.

The iron-containing precipitate formed in this step preferably comprises ferrihydride as a main component. It is more preferable that such iron-containing precipitate comprise ferrihydride as a main component and be substantially free of beta-iron hydroxide oxide.

Ferric chloride used in this step may be in the form of an anhydrate or hydrate thereof. Alternatively, it may be in the form of an aqueous solution thereof. Ferric chloride of any form can be used in the method of the present invention.

An aqueous medium used in this step is preferably water. In such a case, an aqueous solution containing an iron-containing precipitate, or preferably a precipitate containing ferrihydride as a main component, is generated in this step. Such aqueous medium is preferably substantially free of components other than citric acid and the precipitate described above.

Ferric chloride and sodium hydroxide used in this step may have a level of purity that is commonly employed in the art. The molar ratio of ferric chloride to sodium hydroxide is preferably from 1:1 to 1:5, and more preferably from 1:2 to 1:4.

The concentration of iron(III) in ferric chloride in the solution generated in this step is preferably 2% to 6% by weight, and more preferably 3% to 5% by weight. Sodium hydroxide content is preferably 5% to 15% by weight, and more preferably 9% to 11% by weight.

The present inventors studied conditions in which beta-iron hydroxide oxide formation would be inhibited. As a result, The present inventors have discovered that an iron-containing precipitate comprising ferrihydride as a main component and substantially free of beta-iron hydroxide oxide could be formed by bringing ferric chloride into contact with sodium hydroxide for a short period of time at a low temperature.

In this step, the duration during which ferric chloride is allowed to be in contact with sodium hydroxide is preferably within 3 hours, more preferably within 2 hours, further preferably within 1 hour, and particularly preferably within 30 minutes. It is preferable that ferric chloride be brought into contact with sodium hydroxide at a temperature (liquid temperature) of 15° C. or lower, more preferably 10° C. or lower, and particularly preferably from 0° C. to 10° C.

In this step, accordingly, ferric chloride is preferably brought into contact with sodium hydroxide within 3 hours at a liquid temperature of 15° C. or lower, at 10° C. or lower, or from 0° C. to 10° C., more preferably within 2 hours at a liquid temperature of 15° C. or lower, further preferably within 2 hours at a liquid temperature of 10° C. or lower, particularly preferably within 2 hours at a liquid temperature of 0° C. to 10° C., and most preferably within 1 hour at a liquid temperature of 0° C. to 10° C.

The final pH of a mixture obtained by bringing ferric chloride into contact with sodium hydroxide in this step is preferably from 8 to 10.

By performing this step under such conditions, formation of beta-iron hydroxide oxide can be suppressed, and a precipitate substantially free of beta-iron hydroxide oxide can be formed.

2-2. Step of Washing

The method of the present invention may comprise a step of washing comprising washing an iron-containing precipitate 1 to 3 times prior to the step of generating an aqueous solution of iron(III) citrate described below.

In this step, it is preferable that an iron-containing precipitate is washed with an aqueous medium. Such aqueous medium is preferably purified water that is substantially free of other ingredients.

This step is preferably carried out at 10° C. to 30° C.

By performing this step under such conditions, the purity of resulting iron(III) citrate can be enhanced.

2-3. Step of Generating Aqueous Solution of Iron(III) Citrate

This step is intended to generate an aqueous solution of iron(III) citrate by bringing citric acid into contact with the iron-containing precipitate obtained by the above step in an aqueous medium. An example of "contact" is a reaction between an iron-containing precipitate and an aqueous solution of citric acid, but not limited thereto.

An aqueous medium used in this step is preferably water. In such a case, an aqueous solution of iron(III) citrate is generated in this step. Such aqueous medium is preferably substantially free of components other than citric acid and the precipitate described above.

Citric acid used in this step may have a level of purity that is commonly employed in the art. The molar ratio of iron(III) to citric acid contained in the iron-containing precipitate is preferably from 1:1.0 to 1:1.5, and more preferably from 1:1.2 to 1:1.3. According to another embodiment, the molar ratio of iron(III) to citric acid contained in the iron-containing precipitate is preferably from 1:1.0 to 1:3.0, and more preferably from 1:1.0 to 1:1.6.

In the solution obtained in this step, the concentration of citric acid is preferably from 10% to 40% by weight, and more preferably 20% to 30% by weight.

In this step, citric acid is brought into contact with the iron-containing precipitate in a medium to generate a mixture, and the resulting mixture is then heated to generate an aqueous solution of iron(III) citrate. In this step, heating is preferably carried out at a liquid temperature of 60° C. to 100° C., and more preferably at a liquid temperature of 70° C. to 90° C. The heating duration is preferably from 1 to 3 hours, and more preferably from 1.5 to 2.5 hours.

In this step, accordingly, it is particularly preferable that an aqueous solution of iron(III) citrate be generated by heating the aforementioned mixture at the liquid temperature described above for 1 to 3 hours.

By performing this step under such conditions, an aqueous solution containing iron(III) citrate can be generated at a high yield.

2-4. Step of Precipitating Iron(III) Citrate

This step is intended to precipitate iron(III) citrate by bringing the aqueous solution of iron(III) citrate into contact with an organic solvent.

An example of an organic solvent that can be used in this step is, but is not limited to, a water-miscible organic solvent, such as acetone. An organic solvent is preferably acetone or hydrous acetone.

An organic solvent used in this step may have a level of purity that is commonly employed in the art. The amount of an organic solvent used is preferably 300 to 500 parts by weight, and more preferably 350 to 450 parts by weight, relative to 100 parts by weight of the aqueous solution of iron(III) citrate.

In this step, the aqueous solution of iron(III) citrate is brought into contact with an organic solvent under the above conditions to precipitate the iron(III) citrate. In this step, the precipitation temperature is preferably between 15° C. and 35° C., and more preferably between 20° C. and 30° C. The duration of precipitation is preferably from 0.5 to 2 hours, and more preferably from 0.5 to 1 hour.

The iron(III) citrate obtained by the above method may be subjected to an application of interest in that state. Alternatively, precipitated iron(III) citrate may be further dried. For example, drying can be carried out by the method described in Patent Document 1.

By performing this step under such conditions, high-purity iron(III) citrate can be precipitated at a high yield.

3. Medical Use of Iron(III) Citrate 3-1. Pharmaceutical Composition

A pharmaceutical composition comprising, as an active ingredient, the iron(III) citrate of the present invention can be administered to a human and a non-human animal having diseases or disorders described below in vivo. It can be administered to a human a pharmaceutical composition or pharmaceutical formulation in a form described below. When such pharmaceutical composition is administered to a non-human animal, preferable examples thereof include, but are not limited to, a mouse, rat, hamster, guinea pig, rabbit, cat, dog, pig, cow, horse, sheep, and monkey.

Administration of the pharmaceutical composition or pharmaceutical formulation of the present invention to the target (a patient or test subject) enables treatment or amelioration of diseases or disorders described below. Accordingly, the present invention relates to the iron(III) citrate for use as a medicament. In addition, the present invention provides a method for treatment or amelioration of diseases or disorders described below comprising administering the pharmaceutical composition or pharmaceutical formulation of the present invention to the patient or test subject.

For example, the pharmaceutical composition of the present invention can be used in inhibition of absorption of phosphate ingested by a patient or in treatment or amelioration of hyperphosphatemia, but are not limited thereto. Accordingly, the present invention relates to the iron(III) citrate for use in treatment or amelioration of hyperphosphatemia. In addition, the present invention provides an agent for treatment or amelioration of hyperphosphatemia comprising, as an active ingredient, the iron(III) citrate. Also, the present invention provides an agent for reducing serum phosphorus level comprising, as an active ingredient, the iron(III) citrate.

The iron(III) citrate of the present invention has a large specific surface area and it thus has a high capacity for phosphorus adsorption. Accordingly, the present invention provides a phosphate binder comprising, as an active ingredient, the iron(III) citrate of the present invention.

Use of the pharmaceutical composition or pharmaceutical formulation according to the present invention enables treatment or amelioration of the diseases or disorders described above. The term "treatment of hyperphosphatemia" used herein is also defined as "amelioration of hyperphosphatemia." For example, the term refers to reduction of the serum phosphorus level to 3.5 to 6.0 mg/dL, although it is not limited thereto.

3-2. Pharmaceutical Formulation

The iron(III) citrate produced by the method of the present invention; i.e., a pharmaceutical composition comprising, as an active ingredient, high-purity iron(III) citrate of the present invention, may be administered to a subject in the form of the pharmaceutical composition alone. Alternatively, high-purity iron(III) citrate of the present invention can be provided in the form of a medicament (e.g., a pharmaceutical formulation) comprising such compound in combination with at least one member selected from among a pharmaceutically acceptable carrier, an excipient, a disintegrator, a binder, a fluidizing agent, a diluent, a filler, a buffer, an adjuvant, a stabilizer, a preservative, a lubricant, a solvent, a solubilizer, a suspending agent, an isotonizing agent, a soothing agent and other materials known in the art, and, according to need, other drugs. Therefore, the present invention not only provides pharmaceutical compositions described above. The present invention also provides a method for producing a medicament comprising mixing high-purity iron(III) citrate of the present invention with at least one member selected from among a pharmaceutically acceptable carrier, an excipient, a disintegrator, a binder, a fluidizing agent, a diluent, a filler, a buffer, an adjuvant, a stabilizer, a preservative, a lubricant, a solvent, a solubilizer, a suspending agent, an isotonizing agent, a soothing agent and other materials known in the art, and, according to need, other drugs.

Also, the present invention provides use of high-purity iron(III) citrate of the present invention in the manufacture of a medicament for treatment or amelioration of the diseases or disorders described above.

The term "pharmaceutically acceptable substance" used herein refers to a compound, material, composition, and/or dosage form, which yields an adequate benefit/risk ratio within the scope of appropriate medical decision, which does not cause excessive toxicity, stimulation, allergic reactions, or complications, and which is suitable for use while in contact with tissue of a subject (e.g., a human). Since a carrier, an excipient, and the like can be present together with other ingredients of a pharmaceutical formulation, such substance should be "acceptable."

A pharmaceutical formulation can be adequately provided in unit dosage form and it can be prepared by any method well-known in the field of pharmaceutical technology. Such method comprises a step of mixing high-purity iron(III) citrate of the present invention with at least one auxiliary ingredient (e.g., a carrier). In general, a pharmaceutical formulation is prepared by homogeneously and coherently mixing an active compound with a finely ground solid carrier and/or a liquid carrier and then generating a product, according to need.

Examples of forms of pharmaceutical formulations (dosage forms) include, but are not limited to, oral formulations, such as tablets, capsules, granules, powders, troches, syrup agents, emulsions, and suspending agents.

Tablets can be produced by optionally adding to high-purity iron(III) citrate of the present invention at least one auxiliary ingredient described above by a conventional means, such as compression or molding. Compressed tablets can be produced by mixing high-purity iron(III) citrate of the present invention with at least one member selected from among a binder (e.g., povidone, gelatin, acacia gum, sorbitol, Tragacanth, or hydroxypropyl methylcellulose), a filler or diluent (e.g., microcrystalline cellulose or lactose), a lubricant (e.g., calcium stearate, talc, or silica), a disintegrator (e.g., crospovidone, sodium carboxymethyl starch, or crosslinked carboxymethylcellulose sodium), a surfactant, a powder, or wetting agent (e.g., sodium lauryl sulfate), and a preservative (e.g., methyl p-hydroxybenzoate, propyl p-hydroxybenzoate, or sorbic acid), according to need, and compressing the resultant with a suitable machine. Tablets may be optionally coated or incised. Alternatively, tablets may be prepared so as to achieve sustained release or controlled release of iron(III) citrate contained therein, for example. Enteric coating may be optionally applied to tablets, so that iron(III) citrate can be released at a region of the gastrointestinal tract other than the stomach.

3-3. Treatment Method

When the pharmaceutical composition or pharmaceutical formulation of the present invention is used in treatment or amelioration of the diseases or disorders described above, an adequate dose of high-purity iron(III) citrate of the present invention may differs for each patient. In general, a dose is selected so as to achieve a local concentration that realizes desired effects without substantially causing any harmful side effects at a site of interest. A dose selected herein is not limited. For example, it depends on various factors, including activity of iron(III) citrate, the administration route, the administration time, the discharge speed, the duration of treatment, other drugs to be used in combination therewith, and age, gender, body weight, pathological conditions, general health conditions, and anamnesis of a patient.

In vivo administration can be continuously or intermittently (e.g., divisional administration at adequate intervals) carried out with a single dose throughout the entire course of treatment. Administration can be implemented once or several times at dosage levels and patterns that are selected by a physician who provides treatment. When it is orally administered to an adult patient, for example, a suitable dose of iron(III) citrate is generally about 1 g to 8 g per day. Such dose can be administered once or a plurality of times.

EXAMPLES

Hereafter, the present invention is described in greater detail with reference to the examples. It should be noted that the technical scope of the present invention is not limited to these examples.

1. Preparation of Iron(III) Citrate

Example 1

Step of Forming Iron-Containing Precipitate

An aqueous solution of ferric chloride (60.5 kg, 6.7 kg in terms of $Fe^{3+}$, 120.0 mol) was introduced into a reaction vessel and diluted with 102.9 kg of purified water to obtain an aqueous solution of ferric chloride containing 4.1% by weight of $Fe^{3+}$. The aqueous solution of ferric chloride was cooled to a liquid temperature of 0° C. to 5° C. An aqueous solution of 10% by weight of NaOH (139.6 kg) that had been cooled to 0° C. to 5° C. in advance was added dropwise to the aqueous solution of ferric chloride over a period of 120 minutes while maintaining the liquid temperature at 0° C. to 4.2° C., and the final pH level was adjusted to 9.05. After the completion of dropwise addition, the obtained mixture was agitated at 1.6° C. to 3.8° C. (liquid temperature) for 1 hour. The pH level of the mixture was found to be between 8.0 and 10.0.

Step of Washing

The mixture obtained in the step above was washed with 120 kg of purified water with filtration. An iron-containing crude precipitate mainly composed of ferrihydride separated via filtration (i.e., a wet solid (1), 70.52 kg) was agitated and washed in 162.7 kg of purified water for 55 minutes. The suspension was filtered again to obtain an iron-containing precipitate mainly composed of ferrihydride (i.e., a wet solid (2), 53.26 kg).

Step of Generating Aqueous Solution of Iron(III) Citrate

Citric acid (28.9 kg, 150.5 mol) was dissolved in 38.74 kg of purified water to prepare an aqueous solution of citric acid (67.64 kg). The wet solid (2) obtained in the step above (53.26 kg) and the aqueous solution of citric acid above (67.64 kg) were introduced into a reaction vessel, and the mixture was prepared via slow agitation at room temperature (about 25° C.) for 70 minutes at an agitation speed of about 67 rpm. Subsequently, the mixture was slowly heated to a temperature (liquid temperature) of 80° C. in such a manner that the difference between the temperature (liquid temperature) of the mixture and the external temperature was between 0° C. and 15° C. Thereafter, the mixture was agitated at a liquid temperature of 80.1° C. to 84.0° C. for 120 minutes to dissolve the iron-containing precipitate mainly composed of ferrihydride. After such dissolution had been confirmed, the mixture was cooled to a liquid temperature of 20° C. to 30° C. Insoluble material in the resulting mixture was removed by filtration to obtain an aqueous solution of iron(III) citrate (118.0 kg).

Step of Precipitating Iron(III) Citrate

Acetone (471.8 kg, 95% by weight) (i.e., acetone containing 5% water by weight) was introduced into a reaction vessel. The aqueous solution of iron(III) citrate obtained in the step above (118.0 kg) was added dropwise to 95% by weight of acetone in the reaction vessel over a period of 25 minutes with agitation. After the completion of dropwise addition, the obtained mixture was agitated at a liquid temperature of 21.1° C. to 22.2° C. for 40 minutes. The resulting mixture was filtered to obtain an iron(III) citrate-containing precipitate (i.e., a wet solid (3), 74.08 kg). The obtained wet solid (3) (74.08 kg) was dried to obtain high-purity iron(III) citrate of interest in a powdered state (yield: 25.86 kg; 78.86%).

Example 2

Iron(III) citrate of Example 2 was prepared in the same manner as in Example 4, except that an aqueous NaOH solution was added dropwise to the aqueous solution of ferric chloride over a period of 165 minutes while maintaining the liquid temperature between 4.0° C. and 4.7° C., and the final pH level was adjusted to 9.20 in the step of forming the iron-containing precipitate of Example 4 (yield: 136.03 kg, 85.3%).

Example 3

Iron(III) citrate of Example 3 was prepared in the same manner as in Example 4, except that an aqueous NaOH solution was added dropwise to the aqueous solution of ferric chloride over a period of 165 minutes while maintaining the liquid temperature between 4.0° C. and 4.7° C., and the final pH level was adjusted to 9.20 in the step of forming the iron-containing precipitate of Example 4 (yield: 136.42 kg, 84.7%).

Example 4

Step of Forming Iron-Containing Precipitate

An aqueous solution of ferric chloride (639.5 kg, 67.3 kg in terms of $Fe^{3+}$, 1,205 mol) was introduced into a reaction vessel and diluted with 1,002 kg of purified water to obtain an aqueous solution of ferric chloride containing 4.1% $Fe^{3+}$ by weight. The aqueous solution of ferric chloride was cooled to a liquid temperature of 0° C. to 5° C. An aqueous solution containing 10% NaOH by weight (1467.9 kg) that had been cooled to 0° C. to 5° C. in advance was added dropwise to the aqueous solution of ferric chloride over a period of 120 minutes while maintaining the liquid temperature at 3.5° C. to 8.0° C., and the final pH level was adjusted to 9.22. After the completion of dropwise addition, the obtained mixture was agitated at 3.7° C. to 4.7° C. (liquid temperature) for 1 hour. The pH level of the mixture was found to be between 8.0 and 10.0.

Step of Washing

The mixture obtained in the step above was washed with 2,000 l of purified water with filtration. An iron-containing crude precipitate mainly composed of ferrihydride separated via filtration (i.e., a wet solid (1), 628.02 kg) was agitated and washed in 1,627.0 kg of purified water for 25 minutes. The suspension was filtered again to obtain an iron-containing precipitate mainly composed of ferrihydride (i.e., a wet solid (2), 530.75 kg).

Step of Generating Aqueous Solution of Iron(III) Citrate

Citric acid (289.30 kg, 1,506 mol) was dissolved in 389.0 kg of purified water to prepare an aqueous solution of citric acid (678.3 kg). The wet solid (2) obtained in the step above (530.75 kg) and the aqueous solution of citric acid above (678.3 kg) were introduced into a reaction vessel, and the mixture was prepared via slow agitation at room temperature (about 25° C.) for 69 minutes at an agitation speed of about 50 rpm. Subsequently, the mixture was slowly heated to a temperature (liquid temperature) of 80° C. in such a manner that the difference between the temperature (liquid temperature) of the mixture and the external temperature was between 0° C. and 15° C. Thereafter, the mixture was agitated at a liquid temperature of 80.0° C. to 81.9° C. for 120 minutes to dissolve the iron-containing precipitate mainly composed of ferrihydride. After such dissolution had been confirmed, the mixture was cooled to a liquid temperature of 20° C. to 30° C. Insoluble material in the resulting mixture was removed by filtration to obtain an aqueous solution of iron(III) citrate (1,226.5 kg).

Step of Precipitating Iron(III) Citrate

Acetone (2,453 kg) was introduced into a reaction vessel. The aqueous solution of iron(III) citrate obtained in the step above (613.2 kg) was added dropwise to acetone in the reaction vessel over a period of 45 minutes with agitation. After the completion of dropwise addition, the obtained mixture was agitated at a liquid temperature of 24.0° C. to 24.6° C. for 40 minutes. The resulting mixture was filtered to obtain an iron(III) citrate-containing precipitate (i.e., a wet solid (3), 425.17 kg). The obtained wet solid (3) (425.17 kg) was dried to obtain high-purity iron(III) citrate of interest in a powdered state (yield: 154.21 kg; 91.7%).

Example 5

Iron(III) citrate of Example 5 was prepared in the same manner as in Example 4, except that an aqueous NaOH solution was added dropwise to the aqueous solution of ferric chloride over a period of 120 minutes while maintaining the liquid temperature between 3.5° C. and 8.0° C., and the final pH level was adjusted to 9.22 in the step of forming the iron-containing precipitate of Example 4 (yield: 154.61 kg, 91.9%).

Example 6

Iron(III) citrate of Example 6 was prepared in the same manner as in Example 4, except that an aqueous NaOH solution was added dropwise to the aqueous solution of ferric chloride over a period of 115 minutes while maintaining the liquid temperature between 2.6° C. and 7.5° C., and the final pH level was adjusted to 9.09 in the step of forming the iron-containing precipitate of Example 4 (yield: 154.68 kg, 91.5%).

Example 7

Iron(III) citrate of Example 7 was prepared in the same manner as in Example 4, except that an aqueous NaOH solution was added dropwise to the aqueous solution of ferric chloride over a period of 115 minutes while maintaining the liquid temperature between 2.6° C. and 7.5° C., and the final pH level was adjusted to 9.09 in the step of forming the iron-containing precipitate of Example 4 (yield: 156.09 kg, 92.3%).

Example 8

Iron(III) citrate of Example 8 was prepared in the same manner as in Example 4, except that an aqueous NaOH solution was added dropwise to the aqueous solution of ferric chloride over a period of 162 minutes while maintaining the liquid temperature between 2.4° C. and 8.6° C., and the final pH level was adjusted to 9.21 in the step of forming the iron-containing precipitate of Example 4 (yield: 150.43 kg, 92.1%).

Example 9

Iron(III) citrate of Example 9 was prepared in the same manner as in Example 4, except that an aqueous NaOH solution was added dropwise to the aqueous solution of ferric chloride over a period of 162 minutes while maintaining the liquid temperature between 2.4° C. and 8.6° C., and the final pH level was adjusted to 9.21 in the step of forming the iron-containing precipitate of Example 4 (yield: 152.30 kg, 92.8%).

Example 10

Iron(III) citrate of Example 10 was prepared in the same manner as in Example 4, except that an aqueous NaOH solution was added dropwise to the aqueous solution of ferric chloride over a period of 118 minutes while maintaining the liquid temperature between 2.6° C. and 7.6° C., and the final pH level was adjusted to 9.13 in the step of forming the iron-containing precipitate of Example 4 (yield: 149.47 kg, 88.4%).

Example 11

Iron(III) citrate of Example 11 was prepared in the same manner as in Example 4, except that an aqueous NaOH solution was added dropwise to the aqueous solution of ferric chloride over a period of 118 minutes while maintaining the liquid temperature between 2.6° C. and 7.6° C., and the final pH level was adjusted to 9.13 in the step of forming the iron-containing precipitate of Example 4 (yield: 150.47 kg, 89.0%).

Example 12

Iron(III) citrate of Example 12 was prepared in the same manner as in Example 4, except that an aqueous NaOH solution was added dropwise to the aqueous solution of ferric chloride over a period of 105 minutes while maintaining the liquid temperature between 0° C. and 7.3° C., and the final pH level was adjusted to 8.98 in the step of forming the iron-containing precipitate of Example 4 (yield: 146.06 kg, 87.7%).

Example 13

Iron(III) citrate of Example 13 was prepared in the same manner as in Example 4, except that an aqueous NaOH solution was added dropwise to the aqueous solution of ferric chloride over a period of 105 minutes while maintaining the liquid temperature between 0° C. and 7.3° C., and the final pH level was adjusted to 8.98 in the step of forming the iron-containing precipitate of Example 4 (yield: 146.56 kg, 88.0%).

Example 14

Iron(III) citrate of Example 14 was prepared in the same manner as in Example 4, except that an aqueous NaOH solution was added dropwise to the aqueous solution of ferric chloride over a period of 74 minutes while maintaining the liquid temperature between 1.3° C. and 8.3° C., and the final pH level was adjusted to 8.91 in the step of forming the iron-containing precipitate of Example 4 (yield: 146.01 kg, 88.7%).

Example 15

Iron(III) citrate of Example 15 was prepared in the same manner as in Example 4, except that an aqueous NaOH solution was added dropwise to the aqueous solution of ferric chloride over a period of 74 minutes while maintaining the liquid temperature between 1.3° C. and 8.3° C., and the final pH level was adjusted to 8.91 in the step of forming the iron-containing precipitate of Example 4 (yield: 146.23 kg, 89.6%).

Example 16

Iron(III) citrate of Example 16 was prepared in the same manner as in Example 4, except that an aqueous NaOH solution was added dropwise to the aqueous solution of ferric chloride over a period of 91 minutes while maintaining the liquid temperature between 2.5° C. and 8.4° C., and the final pH level was adjusted to 9.64 in the step of forming the iron-containing precipitate of Example 4 (yield: 142.30 kg, 86.2%).

Example 17

Iron(III) citrate of Example 17 was prepared in the same manner as in Example 4, except that an aqueous NaOH solution was added dropwise to the aqueous solution of ferric chloride over a period of 91 minutes while maintaining the liquid temperature between 2.5° C. and 8.4° C., and the final pH level was adjusted to 9.64 in the step of forming the iron-containing precipitate of Example 4 (yield: 144.60 kg, 86.5%).

Example 18

Iron(III) citrate of Example 18 was prepared in the same manner as in Example 4, except that an aqueous NaOH solution was added dropwise to the aqueous solution of ferric chloride over a period of 117 minutes while maintaining the liquid temperature between 1.9° C. and 8.0° C., and the final pH level was adjusted to 8.40 in the step of forming the iron-containing precipitate of Example 4 (yield: 138.93 kg, 86.8%).

Example 19

Iron(III) citrate of Example 19 was prepared in the same manner as in Example 4, except that an aqueous NaOH solution was added dropwise to the aqueous solution of ferric chloride over a period of 117 minutes while maintaining the liquid temperature between 1.9° C. and 8.0° C., and the final pH level was adjusted to 8.40 in the step of forming the iron-containing precipitate of Example 4 (yield: 132.89 kg, 83.2%).

Example 20

Iron(III) citrate of Example 20 was prepared in the same manner as in Example 4, except that an aqueous NaOH solution was added dropwise to the aqueous solution of ferric chloride over a period of 77 minutes while maintaining the liquid temperature between 1.4° C. and 8.3° C., and the final pH level was adjusted to 8.61 in the step of forming the iron-containing precipitate of Example 4 (yield: 146.18 kg, 87.8%).

Example 21

Iron(III) citrate of Example 21 was prepared in the same manner as in Example 4, except that an aqueous NaOH solution was added dropwise to the aqueous solution of ferric chloride over a period of 77 minutes while maintaining the liquid temperature between 1.4° C. and 8.3° C., and the final pH level was adjusted to 8.61 in the step of forming the iron-containing precipitate of Example 4 (yield: 145.92 kg, 89.3%).

Example 22

Iron(III) citrate of Example 22 was prepared in the same manner as in Example 4, except that an aqueous NaOH solution was added dropwise to the aqueous solution of ferric chloride over a period of 76 minutes while maintaining the liquid temperature between 2.2° C. and 9.1° C., and the final pH level was adjusted to 9.08 in the step of forming the iron-containing precipitate of Example 4 (yield: 156.90 kg, 93.7%).

Example 23

Iron(III) citrate of Example 23 was prepared in the same manner as in Example 4, except that an aqueous NaOH solution was added dropwise to the aqueous solution of ferric chloride over a period of 76 minutes while maintaining the liquid temperature between 2.2° C. and 9.1° C., and the final pH level was adjusted to 9.08 in the step of forming the iron-containing precipitate of Example 4 (yield: 153.60 kg, 90.4%).

Example 24

Step of Forming Iron-Containing Precipitate

An iron-containing precipitate was obtained from the mixture prepared in the same manner as in Example 4, except that an aqueous solution of ferric chloride (186.2 g, 24.6 g in terms of $Fe^{3+}$, 0.440 mol) was used as a starting material, an aqueous NaOH solution was added dropwise to the aqueous solution of ferric chloride over a period of 100 minutes while maintaining the liquid temperature between 3.0° C. and 5.3° C., and the final pH level was adjusted to 9.08. High-purity iron(III) citrate of interest was obtained (yield: 24.76 g, 90.6%) in the same manner as in the step of generating an aqueous solution of iron(III) citrate and the step of precipitating iron(III) citrate of Example 4, except that the iron-containing precipitate divided into quarters was used as a starting material and the amount of citric acid was equal to that of $Fe^{3+}$ in the step of generating an aqueous solution of iron(III) citrate.

Example 25

Iron(III) citrate of Example 25 was prepared in the same manner as in Example 20, except that the iron-containing precipitate obtained in Example 20 was used and the amount of citric acid was 2.50 times greater than that of $Fe^{3+}$ in the step of generating an aqueous solution of iron(III) citrate of Example 20 (yield: 26.79 g, 93.7%).

Example 26

Iron(III) citrate of Example 26 was prepared in the same manner as in Example 20, except that the iron-containing precipitate obtained in Example 20 was used and the amount of citric acid was 2.50 times greater than that of $Fe^{3+}$ in the step of generating an aqueous solution of iron(III) citrate of Example 20 (yield: 26.88 g, 93.8%).

Example 27

Iron(III) citrate of Example 27 was prepared in the same manner as in Example 20, except that the iron-containing precipitate obtained in Example 20 was used and the amount of citric acid was 3.00 times greater than that of $Fe^{3+}$ in the step of generating an aqueous solution of iron(III) citrate of Example 20 (yield: 27.96 g, 94.4%).

Example 28

Iron(III) citrate of Example 28 was prepared in the same manner as in Example 20, except that an aqueous NaOH solution was added dropwise to the aqueous solution of ferric chloride over a period of 89 minutes while maintaining the liquid temperature between 2.3° C. and 6.3° C., and the final pH level was adjusted to 9.13 in the step of forming iron-containing precipitate and the amount of citric acid was 1.10 times greater than that of $Fe^{3+}$ in the step of generating an aqueous solution of iron(III) citrate of Example 20 (yield: 37.05 g, 94.8%).

Example 29

Iron(III) citrate of Example 29 was prepared in the same manner as in Example 20, except that an aqueous NaOH solution was added dropwise to the aqueous solution of ferric chloride over a period of 97 minutes while maintaining the liquid temperature between 0° C. and 5.9° C., and the final pH level was adjusted to 9.25 in the step of forming iron-containing precipitate and the amount of citric acid was 1.25 times greater than that of $Fe^{3+}$ in the step of generating an aqueous solution of iron(III) citrate of Example 20 (yield: 37.98 g, 93.5%).

Example 30

Iron(III) citrate of Example 30 was prepared in the same manner as in Example 20, except that an aqueous NaOH solution was added dropwise to the aqueous solution of ferric chloride over a period of 91 minutes while maintaining the liquid temperature between 3.1° C. and 6.3° C., and the final pH level was adjusted to 9.21 in the step of forming iron-containing precipitate and the amount of citric acid was 1.40 times greater than that of $Fe^{3+}$ in the step of generating an aqueous solution of iron(III) citrate of Example 20 (yield: 37.15 g, 94.5%).

Example 31

Iron(III) citrate of Example 31 was prepared in the same manner as in Example 20, except that an aqueous NaOH solution was added dropwise to the aqueous solution of ferric chloride over a period of 90 minutes while maintaining the liquid temperature between 3.7° C. and 5.4° C., and the final pH level was adjusted to 9.28 in the step of forming iron-containing precipitate and the amount of citric acid was 1.55 times greater than that of $Fe^{3+}$ in the step of generating an aqueous solution of iron(III) citrate of Example 20 (yield: 37.69 g, 96.8%).

Comparative Examples 1-4

An iron(III) citrate was prepared in accordance with the method described in Patent Document 1. However, conditions of a step corresponding to the step of forming iron-containing precipitate according to the present invention were modified as shown in Table 3 below.

Comparative Example 11

A commercially available iron(III) citrate for food additives was used (Kanto Kagaku; production lot number: 901X1445; date of production: January, 2007). Such iron (III) citrate is prepared by allowing ferric sulfate to react with ferric hydroxide prepared from ammonia water and with citric acid, concentrating the resulting solution to prepare a syrup, applying the syrup thinly to a glass plate, and drying the resultant until a small lamina is peeled therefrom (the guidelines for Japanese Standards of Food Additives).

Comparative Example 12

A commercially available iron(III) citrate complying with food additive standards was used (SIGMA, technical grade; production lot number: 048K0125; date of production: June, 2008). Such iron(III) citrate is prepared in the same manner as described in Comparative Example 11.

2. Component Analysis of Iron(III) Citrate

The amount of iron(III) (via the titration method), the amount of citric acid (via liquid chromatography), and the amount of moisture (via the Karl Fischer method, coulometric titration; standard test code: B-021) were measured for iron(III) citrates of Comparative Examples 11 and 12 and Examples 1 to 31 in accordance with conventional techniques. The results are shown in Table 1A and Table 1B.

TABLE 1A

Results of component analysis of iron(III) citrates of Comparative Examples

| Comparative Examples | Amount of iron(III) (wt. %) | Amount of citric acid (wt. %) | Amount of water (wt. %) | Molar ratio of iron(III) to citric acid | Molar ratio of iron(III) to water |
|---|---|---|---|---|---|
| 11 | 17.6 | 66.7 | 16.7 | 1:1.102 | 1:2.941 |
| 12 | 17.8 | 67.6 | 14.1 | 1:1.104 | 1:2.455 |
| Average | 17.7 | 67.2 | 15.4 | 1:1.10 | 1:2.70 |

TABLE 1B

Results of component analysis of iron(III) citrates of Examples

| Examples | Amount of iron(III) (wt. %) | Amount of citric acid (wt. %) | Amount of water (wt. %) | Molar ratio of iron(III) to citric acid | Molar ratio of iron(III) to water |
|---|---|---|---|---|---|
| 1 | 20.3 | 60.2 | 18.3 | 1:0.862 | 1:2.794 |
| 2 | 21.0 | 59.7 | 18.6 | 1:0.826 | 1:2.745 |
| 3 | 20.8 | 59.4 | 19.1 | 1:0.830 | 1:2.846 |
| 4 | 20.0 | 60.6 | 18.7 | 1:0.881 | 1:2.898 |
| 5 | 20.0 | 60.5 | 18.8 | 1:0.879 | 1:2.913 |
| 6 | 19.9 | 60.1 | 19.4 | 1:0.878 | 1:3.021 |
| 7 | 19.9 | 60.1 | 19.3 | 1:0.878 | 1:3.006 |
| 8 | 19.6 | 59.7 | 18.1 | 1:0.885 | 1:2.862 |
| 9 | 20.5 | 59.1 | 19.0 | 1:0.838 | 1:2.873 |
| 10 | 19.9 | 61.1 | 17.9 | 1:0.893 | 1:2.788 |
| 11 | 19.9 | 60.9 | 18.5 | 1:0.890 | 1:2.881 |
| 12 | 20.2 | 61.5 | 17.4 | 1:0.885 | 1:2.670 |
| 13 | 20.2 | 60.9 | 17.8 | 1:0.876 | 1:2.731 |
| 14 | 20.5 | 60.3 | 18.6 | 1:0.855 | 1:2.812 |
| 15 | 20.6 | 60.3 | 18.4 | 1:0.851 | 1:2.768 |
| 16 | 20.4 | 61.3 | 17.1 | 1:0.874 | 1:2.598 |
| 17 | 20.1 | 60.4 | 18.4 | 1:0.874 | 1:2.837 |
| 18 | 20.8 | 60.8 | 17.3 | 1:0.850 | 1:2.578 |
| 19 | 21.2 | 61.0 | 16.5 | 1:0.836 | 1:2.412 |
| 20 | 20.2 | 61.1 | 17.5 | 1:0.879 | 1:2.685 |
| 21 | 20.3 | 61.1 | 17.2 | 1:0.875 | 1:2.626 |
| 22 | 19.9 | 60.4 | 18.5 | 1:0.882 | 1:2.881 |
| 23 | 20.2 | 61.5 | 17.8 | 1:0.885 | 1:2.731 |
| 24 | 21.4 | 58.9 | — | 1:0.800 | — |
| 25 | 18.1 | 65.6 | — | 1:1.054 | — |
| 26 | 18.3 | 65.8 | — | 1:1.045 | — |
| 27 | 17.6 | 66.5 | — | 1:1.098 | — |
| 28 | 21.4 | 58.6 | — | 1:0.796 | — |
| 29 | 20.1 | 60.3 | — | 1:0.872 | — |
| 30 | 20.3 | 60.9 | — | 1:0.872 | — |
| 31 | 20.0 | 61.5 | — | 1:0.894 | — |
| Maximum | 21.4 | 66.5 | 19.4 | 1:1.098 | 1:3.021 |
| Minimum | 17.6 | 58.6 | 16.5 | 1:0.796 | 1:2.412 |
| Average | 20.1 | 61.0 | 18.2 | 1:0.884 | 1:2.781 |

As shown in Table 1A, the average molar ratio of iron(III) to citric acid in iron(III) citrates of Comparative Examples 11 and 12 was 1:1.10, and the average molar ratio of iron(III) to water was 1:2.70.

In contrast, the amounts of iron(III), citric acid, and water in iron(III) citrates of Examples 1 to 31 were 17.6% to 21.4% by weight, 58.6% to 66.5% by weight, and 16.5% to 19.4% by weight, respectively, based on the total weight of iron(III) citrate, as shown in Table 1B. That is, no remarkable differences were observed in the measurement results for the examples. The molar ratio of iron(III) to citric acid determined based on the measured value above was 1:0.796 to 1:1.098, and the molar ratio of iron(III) to water was 1:2.412 to 1:3.021.

The maximal and minimal molar ratios of Examples 1 to 31 were applied to the molecular formula "Fe.x($C_6H_8O_7$).y($H_2O$)." As a result, the range of x was found to be from 0.796 to 1.098, and that of y was found to be from 2.412 to 3.021.

3. Elemental Analysis of Iron(III) Citrate

Iron(III) citrates of Comparative Examples 11 and 12 and Examples 1 to 23 were subjected to elemental analysis in accordance with a conventional technique to measure the amount of carbon, the amount of hydrogen, and the amount of oxygen. The results are shown in Table 2A and Table 2B.

TABLE 2A

Results of elemental analysis of iron(III) citrates of Comparative Examples

| Comparative Examples | Amount of carbon (wt. %) | Amount of hydrogen (wt. %) | Amount of oxygen (wt. %) | Amount of iron(III)[1] (wt. %) | Compositional ratio of iron(III) to carbon | Compositional ratio of iron(III) to hydrogen | Compositional ratio of iron(III) to oxygen |
|---|---|---|---|---|---|---|---|
| 11 | 25.1 | 3.5 | 52.1 | 17.6 | 1:6.63 | 1:11.02 | 1:10.33 |
| 12 | 26.0 | 3.3 | 51.3 | 17.8 | 1:6.79 | 1:10.27 | 1:10.06 |
| Average | 25.6 | 3.4 | 51.7 | 17.7 | 1:6.7 | 1:10.6 | 1:10.2 |

[1]Values are reproduced from Table 1A "Amount of iron(III) (wt. %)"

TABLE 2B

Results of elemental analysis of iron(III) citrates of Examples

| Examples | Amount of carbon (wt. %) | Amount of hydrogen (wt. %) | Amount of oxygen (wt. %) | Amount of iron(III)[1] (wt. %) | Compositional ratio of iron(III) to carbon | Compositional ratio of iron(III) to hydrogen | Compositional ratio of iron(III) to oxygen |
|---|---|---|---|---|---|---|---|
| 1 | 22.7 | 3.5 | 50.8 | 20.3 | 1:5.20 | 1:9.55 | 1:8.73 |
| 2 | 22.5 | 3.5 | 51.0 | 21.0 | 1:4.98 | 1:9.23 | 1:8.48 |
| 3 | 22.3 | 3.5 | 50.3 | 20.8 | 1:4.98 | 1:9.32 | 1:8.44 |
| 4 | 22.7 | 3.5 | 51.1 | 20.0 | 1:5.28 | 1:9.70 | 1:8.92 |
| 5 | 22.8 | 3.6 | 50.8 | 20.0 | 1:5.30 | 1:9.97 | 1:8.87 |
| 6 | 22.6 | 3.7 | 52.1 | 19.9 | 1:5.28 | 1:10.30 | 1:9.14 |
| 7 | 22.6 | 3.6 | 52.5 | 19.9 | 1:5.28 | 1:10.02 | 1:9.21 |
| 8 | 22.5 | 3.5 | 51.5 | 19.6 | 1:5.34 | 1:9.84 | 1:9.07 |
| 9 | 22.2 | 3.5 | 52.3 | 20.5 | 1:5.04 | 1:9.46 | 1:8.90 |
| 10 | 23.0 | 3.5 | 51.1 | 21.3 | 1:5.02 | 1:9.09 | 1:8.37 |
| 11 | 22.9 | 3.5 | 50.8 | 20.7 | 1:5.14 | 1:9.35 | 1:8.57 |
| 12 | 23.3 | 3.5 | 50.6 | 20.9 | 1:5.18 | 1:9.26 | 1:8.45 |
| 13 | 23.1 | 3.4 | 50.7 | 20.9 | 1:5.14 | 1:9.00 | 1:8.47 |
| 14 | 22.8 | 3.6 | 51.2 | 22.0 | 1:4.82 | 1:9.05 | 1:8.12 |
| 15 | 22.9 | 3.6 | 51.1 | 21.9 | 1:4.86 | 1:9.09 | 1:8.14 |
| 16 | 23.2 | 3.4 | 50.7 | 22.0 | 1:4.90 | 1:8.55 | 1:8.04 |
| 17 | 22.9 | 3.5 | 51.8 | 22.2 | 1:4.80 | 1:8.72 | 1:8.14 |
| 18 | 22.9 | 3.5 | 52.1 | 21.5 | 1:4.95 | 1:9.00 | 1:8.46 |
| 19 | 23.1 | 3.4 | 51.6 | 21.8 | 1:4.93 | 1:8.62 | 1:8.26 |
| 20 | 23.0 | 3.5 | 50.9 | 20.7 | 1:5.17 | 1:9.35 | 1:8.58 |
| 21 | 23.1 | 3.4 | 50.3 | 20.9 | 1:5.14 | 1:9.00 | 1:8.40 |
| 22 | 22.9 | 3.5 | 50.9 | 20.5 | 1:5.19 | 1:9.44 | 1:8.67 |
| 23 | 23.1 | 3.4 | 50.9 | 20.8 | 1:5.16 | 1:9.04 | 1:8.54 |
| Maximum | 23.3 | 3.7 | 52.5 | 22.2 | 1:5.34 | 1:10.30 | 1:9.21 |
| Minimum | 22.2 | 3.4 | 50.3 | 19.6 | 1:4.80 | 1:8.55 | 1:8.04 |
| Average | 22.8 | 3.5 | 51.2 | 20.9 | 1:5.09 | 1:9.30 | 1:8.56 |

[1] Values of Examples 1 to 9 are reproduced from Table 1B "Amount of iron(III) (wt. %)"

As shown in Table 2A, the average compositional ratio of iron(III) to carbon, that of iron(III) to hydrogen, and that of iron(III) to oxygen in iron(III) citrates of Comparative Examples 11 and 12 were 1:6.7, 1:10.6, and 1:10.2, respectively.

In contrast, the average compositional ratio of iron(III) to carbon, that of iron(III) to hydrogen, and that of iron(III) to oxygen in iron(III) citrates of Examples 1 to 23 were 1:5.09, 1:9.30, and 1:8.56, respectively, as shown in Table 2B. The above average compositional ratios were applied to the molecular formula "Fe.x($C_6H_8O_7$).y($H_2O$)," which is an embodiment of iron(III) citrate, the average composition was determined to be "$FeC_{5.09}H_{9.30}O_{8.56}$," and the average molecular weight was determined to be 263.33.

4. Measurement of Infrared Absorption Spectrum of Iron(III) Citrate

Figure 1:
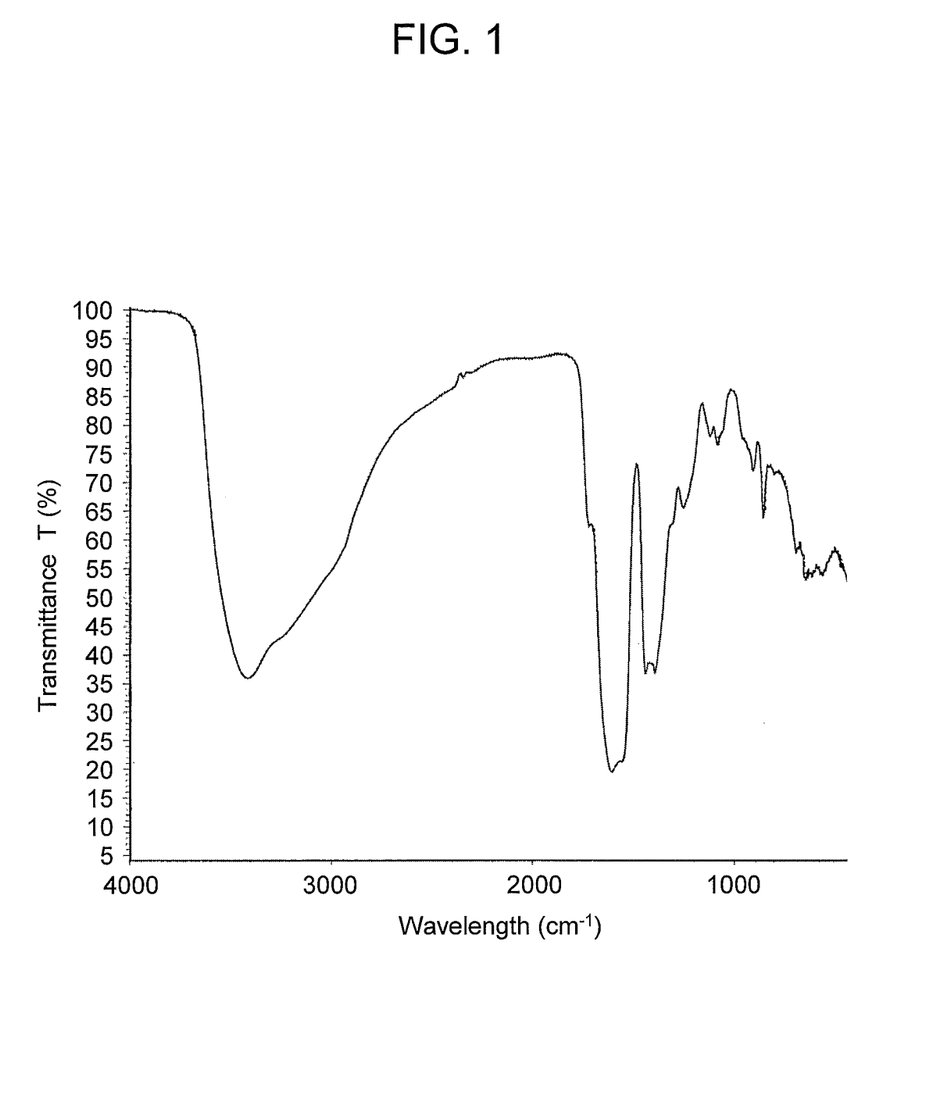
FIG. 1 shows the IR spectrum of the iron(III) citrate of Example 4.

The infrared absorption spectra (the IR spectra) of iron (III) citrates of Examples 1 to 23 were measured using the potassium bromide disk method. FIG. 1 shows the IR spectrum of iron(III) citrate of Example 4.

As shown in FIG. 1, the IR spectrum of iron(III) citrate according to Example 4 demonstrates that a strong absorption deduced to be derived from C=O stretching vibration of dissociated carbonium ions of citric acid was observed at around 1,608 $cm^{-1}$ and a weak absorption deduced to be derived from C=O stretching vibration of non-dissociative carboxylic acid of citric acid was observed at around 1,717 $cm^{-1}$. In addition, iron(III) citrates according to other examples exhibited IR spectral patterns similar to those of the iron(III) citrate of Example 4, and absorption bands of equivalent intensities were observed at regions close to the above wavelength regions.

5. Chemical Structure Analysis of Iron(III) Citrate

As described above, the results of component analysis, elemental analysis, and infrared absorption spectral measurement demonstrate that the chemical structure of iron(III) citrates of Examples 1 to 31 is in the form of a complex represented by the molecular formula: Fe.x($C_6H_8O_7$).y ($H_2O$) (wherein x is from 0.796 to 1.098 and y is from 2.412 to 3.021) instead of a normal salt in which the molar ratio of iron(III) to trivalent citric acid is 1:1.

6. Powder X-Ray Diffraction Analysis of Iron(III) Citrate

Iron(III) citrate of Example 4 was subjected to powder X-ray diffraction analysis to obtain a powder X-ray diffraction spectrum. Cobalt was used as an anticathode. The results are shown in FIG. 2.

Figure 2:
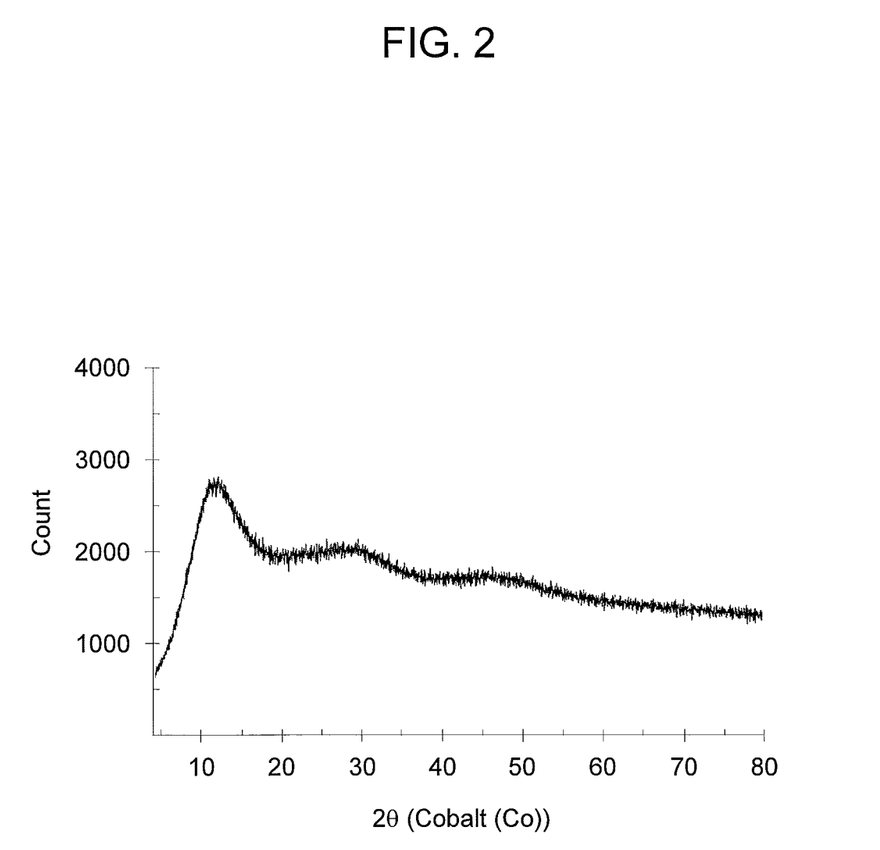
FIG. 2 shows the X-ray diffraction spectrum of the iron(III) citrate powder of Example 4.

As shown in FIG. 2, the powder X-ray diffraction spectrum of iron(III) citrate of Example 4 exhibited a halo pattern having diffusive maxima. Accordingly, iron(III) citrate of Example 4 was determined to be amorphous (amorphous powder).

7. Identification of Beta-Iron Hydroxide Oxide and Quantification of Beta-Iron Hydroxide Oxide In order to qualitatively and quantitatively analyze beta-iron hydroxide oxides that are contaminants of the iron(III) citrates of Examples 1 to 31, the peak area of the diffraction peak at around a diffraction angle of 40 to 41 degrees observed via powder X-ray diffraction (cobalt tube) was determined via the automatic integration method, and the amount of beta-iron hydroxide oxide (% by weight) relative to the total weight of the sample in an iron(III) citrate sample was determined via the external standard method using the formula:

amount of beta-iron hydroxide oxide (% by weight)=
$(Q_T/Q_S) \times 0.025 \times CF$ wherein $Q_T$ represents the peak area of the diffraction peak at around a diffraction angle of 40 to 41 degrees derived from 2.5% beta-iron hydroxide oxide;

$Q_S$ represents the peak area of the diffraction peak at around a diffraction angle of 40 to 41 degrees derived from the sample; and CF represents the content of the standard beta-iron hydroxide oxide (% by weight).

Conditions for performing powder X-ray diffraction analysis are as described below.
Target: Co
X-ray tube current: 40 mA
X-ray tube voltage: 45 kV
Scan field: 2θ=38 to 44 degrees
Step: 2θ=0.01671 degrees
Average time/step: 1000 s
Fixed divergence slit: ½ degrees
Rate of revolution: 60 rpm
Light-receiving filter: Fe filter
Scan axis: Gonio
Anti-scatter slit: 1 degree Test Example 1

Examination of Conditions for Sodium Hydroxide Addition

The influence of the temperature and the duration of sodium hydroxide addition in the step of forming iron-containing precipitate on the production of beta-iron hydroxide oxide and on the solubility of the resulting iron(III) citrate was examined Iron(III) citrates of Examples 1 to 31 were prepared in accordance with the method described in 1 above.

Iron(III) citrates of Comparative Examples 1 to 4 were prepared in accordance with the method described in Patent Document 1 for comparison.

Iron(III) citrates of Comparative Examples 1 to 4 and Examples 1 to 31 were evaluated in terms of the presence or absence of a peak derived from beta-iron hydroxide oxide via powder X-ray diffraction analysis, and solubility in the first fluid of dissolution testing of the Japanese Pharmacopoeia, Fifteenth Edition after 30 minutes via the paddle method according to the Japanese Pharmacopoeia, Fifteenth Edition (paddle method, 100 rpm, 600 mg/900 ml; ultraviolet and visible absorption spectra of the solution are measured and determined based on absorption at maximal wavelength). The results are shown in Table 3.

TABLE 3

Influence of temperature and duration of dropwise addition of sodium hydroxide on generation of beta-iron hydroxide oxide and on solubility of iron(III) citrate

| Comparative Examples/Examples | Conditions for dropwise addition of sodium hydroxide | | Evaluation of iron(III) citrate | |
|---|---|---|---|---|
| | Temperature | Duration | Peak derived from beta-iron hydroxide oxide | Solubility |
| Comparative Example 1 | 26° C. to 28° C. | 1 hour | Observed | 82% |
| Comparative Example 2 | 21° C. to 29° C. | 1 hour and 40 minutes | Observed | 73% |
| Comparative Example 3 | 21° C. to 29° C. | 1 hour and 40 minutes | Observed | 74% |
| Comparative Example 4 | 22° C. to 24° C. | 4 hours | Observed | 79% |
| Example 1 | 0° C. to 4.2° C. | 2 hours | Not observed | 96% |
| Example 2 | 4.0° C. to 4.7° C. | 2 hours and 45 minutes | Observed | 93% |
| Example 3 | 4.0° C. to 4.7° C. | 2 hours and 45 minutes | Observed | 94% |
| Example 4 | 3.5° C. to 8.0° C. | 2 hours | Not observed | 97% |
| Example 5 | 3.5° C. to 8.0° C. | 2 hours | Not observed | 100% |
| Example 6 | 2.6° C. to 7.5° C. | 1 hour and 55 minutes | Not observed | 96% |
| Example 7 | 2.6° C. to 7.5° C. | 1 hour and 55 minutes | Not observed | 97% |
| Example 8 | 2.4° C. to 8.6° C. | 2 hours and 42 minutes | Observed | 94% |
| Example 9 | 2.4° C. to 8.6° C. | 2 hours and 42 minutes | Observed | 95% |
| Example 10 | 2.6° C. to 7.6° C. | 1 hour and 58 minutes | Not observed | 88% |
| Example 11 | 2.6° C. to 7.6° C. | 1 hour and 58 minutes | Not observed | 99% |
| Example 12 | 0° C. to 7.3° C. | 1 hour and 45 minutes | Not observed | 99% |
| Example 13 | 0° C. to 7.3° C. | 1 hour and 45 minutes | Not observed | 102% |
| Example 14 | 1.3° C. to 8.3° C. | 1 hour and 14 minutes | Not observed | 102% |
| Example 15 | 1.3° C. to 8.3° C. | 1 hour and 14 minutes | Not observed | 98% |
| Example 16 | 2.5° C. to 8.4° C. | 1 hour and 31 minutes | Not observed | 95% |
| Example 17 | 2.5° C. to 8.4° C. | 1 hour and 31 minutes | Not observed | 94% |
| Example 18 | 1.9° C. to 8.0° C. | 1 hour and 57 minutes | Not observed | 97% |
| Example 19 | 1.9° C. to 8.0° C. | 1 hour and 57 minutes | Not observed | 98% |
| Example 20 | 1.4° C. to 8.3° C. | 1 hour and 17 minutes | Not observed | 100% |
| Example 21 | 1.4° C. to 8.3° C. | 1 hour and 17 minutes | Not observed | 98% |
| Example 22 | 2.2° C. to 9.1° C. | 1 hour and 16 minutes | Not observed | 100% |
| Example 23 | 2.2° C. to 9.1° C. | 1 hour and 16 minutes | Not observed | 97% |
| Example 24 | 3.0° C. to 5.3° C. | 1 hour and 40 minutes | Not observed | 94% |
| Example 25 | 3.0° C. to 5.3° C. | 1 hour and 40 minutes | Not observed | 101% |
| Example 26 | 3.0° C. to 5.3° C. | 1 hour and 40 minutes | Not observed | 102% |
| Example 27 | 3.0° C. to 5.3° C. | 1 hour and 40 minutes | Not observed | 99% |
| Example 28 | 2.3° C. to 6.3° C. | 1 hour and 29 minutes | Not observed | — |
| Example 29 | 0° C. to 5.9° C. | 1 hour and 37 minutes | Not observed | — |
| Example 30 | 3.1° C. to 6.3° C. | 1 hour and 31 minutes | Not observed | — |
| Example 31 | 3.7° C. to 5.4° C. | 1 hour and 30 minutes | Not observed | — |

In the step of forming iron-containing precipitate, the reaction between ferric chloride and sodium hydroxide is preferably carried out at a temperature (liquid temperature) of 15° C. or lower, more preferably at 10° C. or lower, and particularly preferably at 0° C. to 10° C., as shown in Table 3.

In the step of forming iron-containing precipitate, dropwise addition of sodium hydroxide is preferably completed within 3 hours, more preferably within 2 hours, further preferably within 1 hour, and particularly preferably within 30 minutes.

In the step of forming iron-containing precipitate, accordingly, dropwise addition of sodium hydroxide is preferably completed, for example, within 3 hours at 15° C. or lower, 10° C. or lower, or 0° C. to 10° C., more preferably within 2 hours at 15° C. or lower, further preferably within 2 hours at 10° C. or lower, particularly preferably within 2 hours at 0° C. to 10° C. (liquid temperature), and most preferably within 1 hour at 0° C. to 10° C.

Test Example 2

Quantification of Beta-Iron Hydroxide Oxide

Regarding iron(III) citrates of Comparative Examples 1 to 4 and Examples 1, 4, 5, 6, 7, and 10 to 23, the amount of beta-iron hydroxide oxide (% by weight) relative to the total weight of the sample in an iron(III) citrate sample was determined via powder X-ray diffraction analysis described above. The results are shown in Table 4.

TABLE 4

Beta-iron hydroxide oxide content in iron(III) citrate

|  | Lot number | Beta-iron hydroxide oxide content (wt. %) |
| --- | --- | --- |
| Iron(III) citrate produced by the method of Patent Document 1 | Comparative Example 1 | 6.8 |
|  | Comparative Example 2 | 8.9 |
|  | Comparative Example 3 | 8.3 |
|  | Comparative Example 4 | 7.3 |
| Iron(III) citrate of the invention | Example 1 | Undetectable (1%) |
|  | Example 4 |  |
|  | Example 5 |  |
|  | Example 6 |  |
|  | Example 7 |  |
|  | Examples 10 to 23 |  |

8. Dissolution Profile in the First Fluid of Dissolution Testing of the Japanese Pharmacopoeia The dissolution profiles of iron(III) citrates of Comparative Examples 1, 11, and 12 and Examples 4, 5, 6, 7, 8, and 9 in the first fluid of dissolution testing of the Japanese Pharmacopoeia, Fifteenth Edition (pH 1.2) were compared via the paddle method according to the Japanese Pharmacopoeia, Fifteenth Edition (paddle method, 100 rpm, 600 mg/900 ml). The samples prepared in accordance with the method described above were grounded and used as iron(III) citrates of Comparative Example 1 and Examples 4, 5, 6, 7, 8, and 9. The results are shown in FIG. 3.

Figure 3:
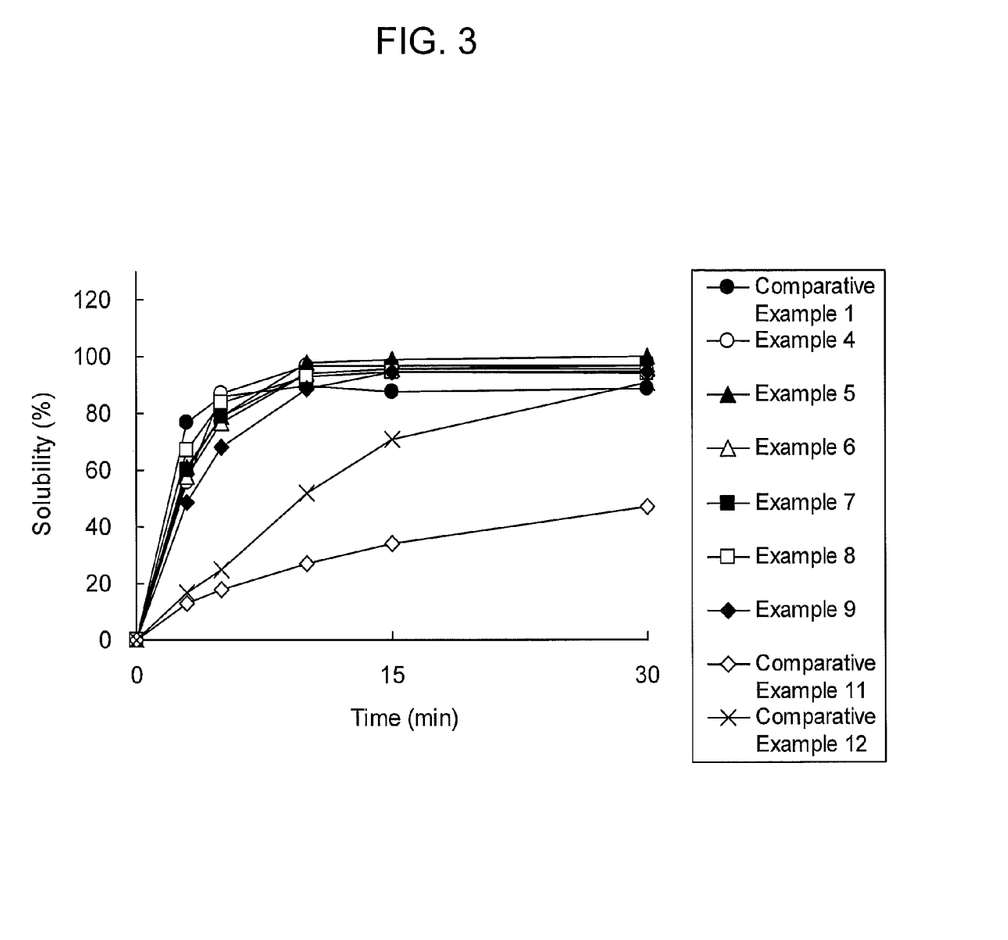
FIG. 3 shows the results of comparison of dissolution profiles determined with the use of the first fluid (pH 1.2) of dissolution testing of the Japanese Pharmacopoeia for the iron(III) citrates according to Comparative Examples 1, 11, and 12 and Examples 4, 5, 6, 7, 8, and 9.

According to an embodiment of the present invention, 95% by weight or more of the iron(III) citrate dissolves in the first fluid of dissolution testing of the Japanese Pharmacopoeia (pH 1.2, paddle method, 100 rpm, 600 mg/900 ml) within 15 minutes, and preferably within 10 minutes, as shown in FIG. 3. In addition, the percentage dissolved within 15 minutes is 80% or more, preferably 85% or more, more preferably 90% or more, and most preferably 95% or more.

9. Measurement of Specific Surface Area

Specific surface areas of iron(III) citrates of Comparative Examples 11 and 12 and Examples 1, 4, 5, 6, 7, and 10 to 23 were measured by nitrogen gas adsorption (relative pressure: 0.05 to 0.3) (BET surface area). The results are shown in Table 5.

TABLE 5

Specific surface area of iron(III) citrate

|  | Lot number | Specific surface area (m$^2$/g) |
| --- | --- | --- |
| Commercially available iron(III) citrate | Comparative Example 11 | 0.80 |
|  | Comparative Example 12 | 0.62 |
| Iron(III) citrate of the invention | Example 1 | 21.8 |
|  | Example 4 | 33.4 |
|  | Example 5 | 31.0 |
|  | Example 6 | 30.4 |
|  | Example 7 | 29.8 |
|  | Example 10 | 29.9 |
|  | Example 11 | 30.0 |
|  | Example 12 | 30.3 |
|  | Example 13 | 29.1 |
|  | Example 14 | 37.9 |
|  | Example 15 | 38.5 |
|  | Example 16 | 33.7 |
|  | Example 17 | 32.4 |
|  | Example 18 | 39.9 |
|  | Example 19 | 39.8 |
|  | Example 20 | 33.8 |
|  | Example 21 | 35.5 |
|  | Example 22 | 32.6 |
|  | Example 23 | 32.8 |

10. Pharmacological Test

Use Example 1

Effects of Inhibiting Phosphorus Absorption in Rats

Figure 4:
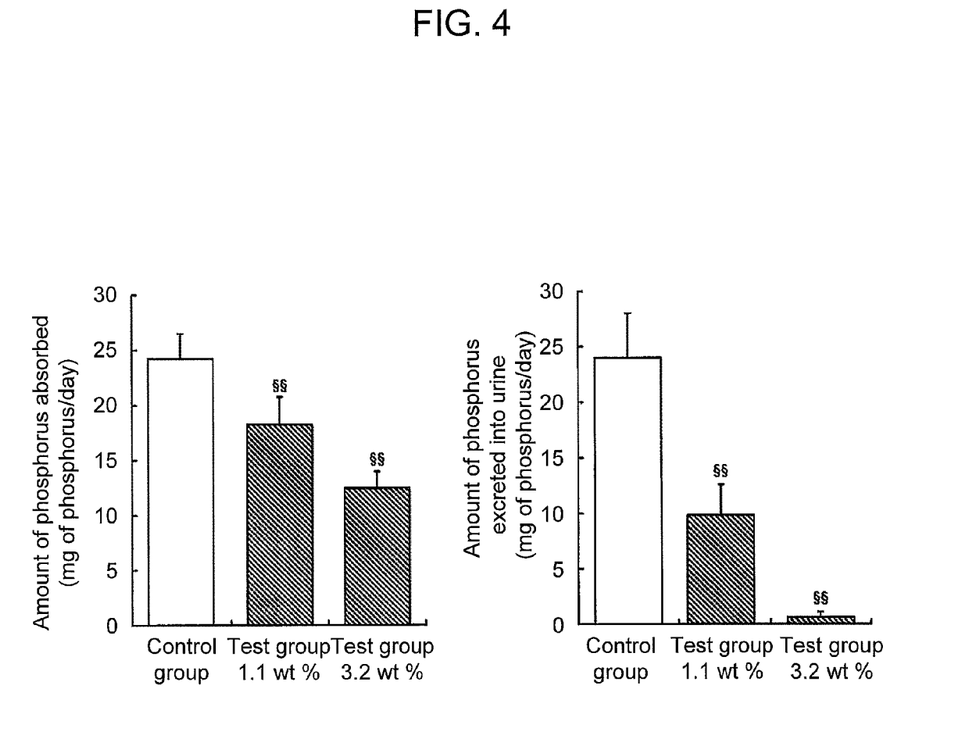
FIG. 4 shows the average amount of phosphorus absorbed and the average amount of phosphorus excreted into the urine (mg/day) of a control group and of a test group (Example 1) determined via a test of phosphorus absorption inhibition using rats.

Effects of the iron(III) citrate (Example 1) for inhibiting phosphorus absorption were examined using rats. A feed mixture comprising the iron(III) citrate of Example 1 at 1.1% by weight or 3.2% by weight based on the total weight of the feed mixture was administered to a group of 8 or 9 male SD rats for 7 days. Feed containing no iron(III) citrate was administered to a control group. Rats were subjected to stool and urine sampling every day during administration. Phosphorus concentrations in the stool and urine samples were measured, and the amounts of phosphorus excreted into the stool and urine were determined. The amount determined by subtracting the amount of iron(III) citrate from the amount of the feed was multiplied by the phosphorus content in the feed to determine the phosphorus intake, and the amount of phosphorus excreted into the stool was subtracted from the phosphorus intake to determine the amount of phosphorus absorbed. FIG. 4 shows the average amounts of phosphorus absorbed and the average amounts of phosphorus excreted into the urine of the control group and of the test group (mg of phosphorus/day).

11. Test of Pharmaceutical Formulation

Formulation Example 1

250-mg Tablet

A graft copolymer of polyvinyl alcohol and polyethylene glycol (1.680 kg, Kollicoat IR, BASF) and a copolymer of polyvinyl alcohol and methyl acrylate or methyl methacrylate (0.42 kg, POVACOAT Type: F; Daido Chemical Industry Co., Ltd.) were added to 25.9 kg of purified water and dissolved with the aid of a propeller mixer to prepare a solution of a binder.

Iron(III) citrate (38.3248 kg, 30 kg in terms of anhydride, mixture of 19.1624 kg each of iron(III) citrates produced in Examples 4 and 5) and 3.4591 kg of crystalline cellulose (Ceolus, PH-102, Asahi Kasei Chemicals Corporation) were introduced into a fluid bed granulator/dryer (WSG-60, Powrex Corp.), and 24.0 kg of the solution of the binder was sprayed for granulation, followed by drying. The resulting dried granules were applied to a screen mill (model: U20, Powrex Corp.) to be sifted through a screen (sieve mesh size: 1,143 μm). Thus, size-regulated powders were obtained.

Low-substituted hydroxypropylcellulose (3.42 kg, LH-11, Shin-Etsu Chemical Co., Ltd.) and 0.57 kg of crospovidone (Kollidon CL-F, BASF) were added to 41.4048 kg of size-regulated powders obtained, and the resultant was mixed using a W-shaped blender (TCW-100, Tokuju Corporation) at 29 rpm for 310 seconds. Subsequently, 0.7752 kg of calcium stearate (Japanese Pharmacopoeia grade, vegetable origin, Taihei Chemical Industrial Co. Ltd.) was added, and the resultant was mixed using a W-shaped blender (TCW-100, Tokuju Corporation) at 29 rpm for 104 seconds to obtain powders for tablet making. The powders for tablet making obtained were applied to a rotary tableting machine (Correct 12 HUK, Kikusui Seisakusho Ltd.) for tablet making at a tablet-making pressure of 950 kgf/punch to obtain capsule-shaped, uncoated tablets with a longer diameter of 14.8 mm, a shorter diameter of 6.8 mm, and a mass of 405 mg.

The resulting uncoated tablets (12.15 kg) were coated with a coating liquid obtained by mixing 600 g of hypromellose (TC-5M, Shin-Etsu Chemical Co., Ltd.), 200 g of titanium oxide (titanium(IV) oxide extra pure, Merck), 100 g of talc (Hi-Filler #17, Matsumura Sangyo Co., Ltd.), 100 g of Macrogol 6000 (Macrogol 6000P, NOF Corporation), and 7,000 g of purified water using an automatic coating machine (HCT-60N, Freund Corporation). Thus, tablets each coated with a film of about 18 mg were obtained (each tablet comprising 12 mg of a graft copolymer of polyvinyl alcohol and polyethylene glycol, 3 mg of a copolymer of polyvinyl alcohol and methyl acrylate or methyl methacrylate, 30 mg of low-substituted hydroxypropylcellulose, and 5 mg of crospovidone).

Compositions of the uncoated tablets and tablets coated with films of Preparation Example 1 are shown in Table 6.

TABLE 6

| Composition of Preparation Example 1 | |
| --- | --- |
| Component | Amount (mg/tablet) |
| Iron(III) citrate (mixture of Example 4 and Example 5) (Weight in terms of anhydride) | 319.4 (250.0) |
| Crystalline cellulose | 28.8 |
| Graft copolymer of polyvinyl alcohol and polyethylene glycol | 12.0 |
| Copolymer of polyvinyl alcohol and methyl acrylate or methyl methacrylate | 3.0 |
| Low-substituted hydroxypropylcellulose | 30.0 |
| Crospovidone | 5.0 |
| Calcium stearate | 6.8 |
| Total of uncoated tablets (weight including moisture in iron(III) citrate) | 405.0 |
| (Weight excluding moisture in iron(III) citrate) | (335.6) |
| Hypromellose | 10.8 |
| Titanium oxide | 3.6 |
| Talc | 1.8 |
| Macrogol 6000 | 1.8 |
| Total of tablets coated with films | 18.0 |

INDUSTRIAL APPLICABILITY

The method of the present invention can provide iron(III) citrate with a reduced beta-iron hydroxide oxide content and high-purity iron(III) citrate exhibiting excellent dissolution properties.

The invention claimed is:

1. A method for producing iron(III) citrate comprising:
   a step of forming an iron-containing precipitate comprising bringing ferric chloride into contact with sodium hydroxide in an aqueous medium for a duration of two hours or less at a liquid temperature of 0° C. to 10° C. to form an iron-containing precipitate;
   a step of generating an aqueous solution of iron(III) citrate comprising bringing citric acid into contact with the iron-containing precipitate in an aqueous medium and generating an aqueous solution of iron(III) citrate via heating; and
   a step of precipitating iron(III) citrate comprising bringing the aqueous solution of iron(III) citrate into contact with an organic solvent to precipitate the iron(III) citrate.

2. The method according to claim 1, wherein the step of generating an aqueous solution of iron(III) citrate comprises bringing citric acid into contact with the iron-containing precipitate at a liquid temperature of 60° C. to 100° C.

3. The method according to claim 1, wherein the iron-containing precipitate is ferrihydride.

4. The method according to claim 1, wherein the duration during which ferric chloride is in contact with sodium hydroxide is one hour or less.

5. The method according to claim 1, wherein the duration during which ferric chloride is in contact with sodium hydroxide is 30 minutes or less.

6. The method according to claim 1, wherein the step of forming an iron-containing precipitate comprises bringing ferric chloride into contact with sodium hydroxide in an aqueous medium at a liquid temperature of lower than 10° C.

7. The method according to claim 1, wherein the step of forming an iron-containing precipitate comprises bringing ferric chloride into contact with sodium hydroxide in an aqueous medium at a liquid temperature of 3.5° C. to 8° C.

8. The method according to claim 1, wherein the step of forming an iron-containing precipitate comprises bringing ferric chloride into contact with sodium hydroxide in an aqueous medium at a liquid temperature of 2.6° C. to 7.5° C.

9. The method according to claim 1, wherein the step of forming an iron-containing precipitate comprises bringing ferric chloride into contact with sodium hydroxide in an aqueous medium at a liquid temperature of 2.6° C. to 7.6° C.

10. The method according to claim 1, wherein the step of forming an iron-containing precipitate comprises bringing ferric chloride into contact with sodium hydroxide in an aqueous medium at a liquid temperature of 0° C. to 7.3° C.

11. The method according to claim 1, wherein the step of forming an iron-containing precipitate comprises bringing ferric chloride into contact with sodium hydroxide in an aqueous medium at a liquid temperature of 1.3° C. to 8.3° C.

12. The method according to claim 1, wherein the step of forming an iron-containing precipitate comprises bringing ferric chloride into contact with sodium hydroxide in an aqueous medium at a liquid temperature of 2.5° C. to 8.4° C.

13. The method according to claim 1, wherein the step of forming an iron-containing precipitate comprises bringing ferric chloride into contact with sodium hydroxide in an aqueous medium at a liquid temperature of 1.9° C. to 8.0° C.

14. The method according to claim 1, wherein the step of forming an iron-containing precipitate comprises bringing ferric chloride into contact with sodium hydroxide in an aqueous medium at a liquid temperature of 1.4° C. to 8.3° C.

15. The method according to claim 1, wherein the step of forming an iron-containing precipitate comprises bringing ferric chloride into contact with sodium hydroxide in an aqueous medium at a liquid temperature of 2.2° C. to 9.1° C.

16. The method according to claim 1, wherein the step of forming an iron-containing precipitate comprises bringing ferric chloride into contact with sodium hydroxide in an aqueous medium at a liquid temperature of 3.0° C. to 5.3° C.

* * * * *